United States Patent [19]

Baggiolini et al.

[11] Patent Number: 4,594,432
[45] Date of Patent: Jun. 10, 1986

[54] PROCESS FOR THE SYNTHESIS OF 1α,23(S),25-TRIHYDROXYCHOLECALCIFEROL AND 1α,23(R),25-TRIHYDROXYCHOLECALCIFEROL

[75] Inventors: Enrico G. Baggiolini, North Caldwell; Milan R. Uskokovic, Upper Montclair; Peter M. Wovkulich, Nutley, all of N.J.

[73] Assignee: Hoffman-La Roche Inc., Nutley, N.J.

[21] Appl. No.: 566,103

[22] Filed: Dec. 27, 1983

Related U.S. Application Data

[63] Continuation-in-part of Ser. No. 461,836, Jan. 28, 1983, abandoned.

[51] Int. Cl.$^4$ .................. C07D 319/06; C07D 303/12; C07F 7/04; C07C 35/22
[52] U.S. Cl. ............................. 549/214; 260/397.2; 549/374; 549/554; 556/449; 568/819
[58] Field of Search ............... 549/215, 374, 554, 214; 556/449; 568/819; 260/397.2

[56] References Cited

U.S. PATENT DOCUMENTS 4,360,472 11/1982 DeLuca et al. .................. 260/397.2
4,367,177 1/1983 DeLuca et al. .................. 260/397.2

FOREIGN PATENT DOCUMENTS 0115314 8/1984 European Pat. Off. .................. 819/
2023146 12/1979 United Kingdom ................ 556/449
2089811 6/1982 United Kingdom ................ 568/819

OTHER PUBLICATIONS

Partridge et al., Vitamin D, Chemical, Biochemical and Clinical Endocrinology of Calcium Metabolism, Feb. 1982, pp. 1073-1078.
Baggiolini et al., Vitamin D, Chemical, Biochemical and Clinical Endocrinology of Calcium Metabolism, Feb. 1982, pp. 1089-1094.
Ikekawa et al., J.C.S. Chem. Comm. (1981), pp. 1157-1159.
Napoli et al., Calcif. Tissue Int. 34, (Suppl. 1) S56, p. 1137, (1982).

Primary Examiner—Ethel G. Love
Attorney, Agent, or Firm—Jon S. Saxe; Bernard S. Leon; William G. Isgro

[57] ABSTRACT

The invention is directed to a process and intermediates for the preparation of 1α,23(S),25-trihydroxycholecalciferol and 1α,23(R),25-trihydroxycholecalciferol. The end-products, 1α,23(S),25-trihydroxycholecalciferol and 1α,23(R),25-trihydroxycholecalciferol, are useful for the treatment of disease states which are characterized by insufficient amounts of 1,25 dihydroxycholecalciferol.

22 Claims, No Drawings

PROCESS FOR THE SYNTHESIS OF 1α,23(S),25-TRIHYDROXYCHOLECALCIFEROL AND 1α,23(R),25-TRIHYDROXYCHOLECALCIFEROL

RELATED APPLICATIONS

This application is a continuation-in-part application of U.S. patent application Ser. No. 461,836, filed Jan. 28, 1983, now abandoned.

BRIEF SUMMARY OF THE INVENTION

The invention is directed to a process for the preparation of 1α,23(S),25-trihydroxycholecalciferol of the formula

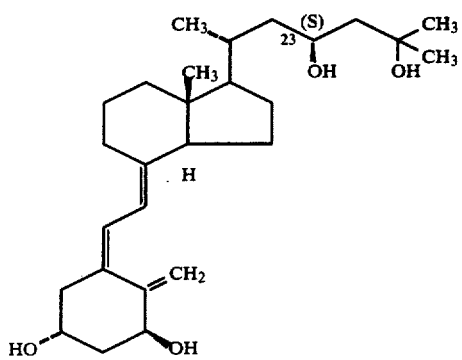

its 23(R) epimer or mixtures thereof,
which comprises the steps of
(a) reacting the corresponding compound of the formula

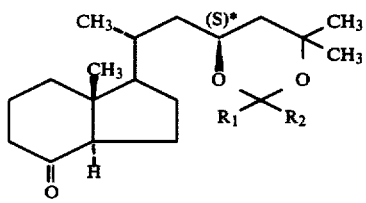

wherein $R^1$ and $R^2$ each, independently, is hydrogen, lower alkyl or aryl, or taken together are lower alkylene of from 3 to 6 carbon atoms
the R* epimer or mixtures thereof,

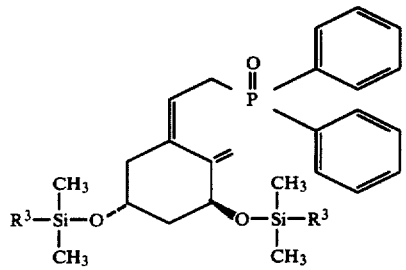

wherein $R^3$ is lower alkyl or aryl,
to yield the corresponding compound of the formula

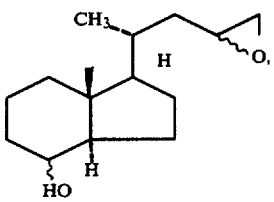

wherein $R^1$, $R^2$ and $R^3$ are as previously described, and
the 23(R) epimer or mixtures thereof, and
(b) removing the protecting groups from a compound of formula IV whereby there is obtained the corresponding compound of formula I.

In another aspect, the invention relates to intermediates of the formula

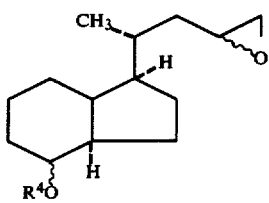

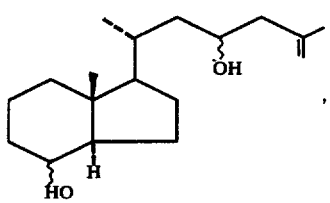

wherein $R^4$ is trilower alkylsilyl, di-lower alkylarylsilyl, lower alkyl-diarylsilyl or triarylsilyl,

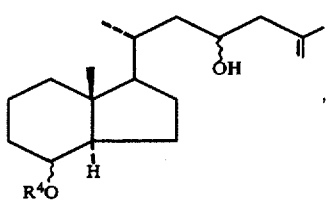

wherein $R^4$ is as previously described,

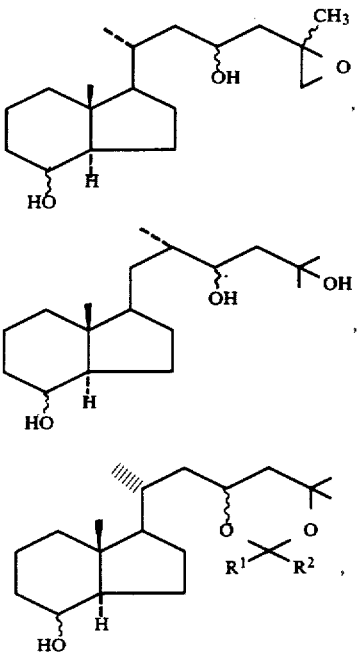

wherein R[1] and R[2] are as above.

DETAILED DESCRIPTION OF THE INVENTION

As used throughout the specification and the appended claims, the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, 1-propyl, tert-butyl, hexyl, heptyl, octyl and the like. The term "lower alkylene" denotes a divalent substituent consisting solely of carbon and hydrogen of from 1 to 8 carbon atoms which may be straight- or branched-chain and whose free valences are attached to two distinct groups. Examples of alkylene groups are methylene, ethylene, propylene, butylene, amylene, hexylene, heptylene, octylene and the like. The term "lower alkoxy" refers to a lower alkyl ether group. Examples of alkoxy groups are methoxy, ethoxy, isopropoxy, tert-butoxy and the like. The term "phenyl-lower alkoxy" refers to a lower alkoxy group which is substituted by a phenyl ring. Examples of phenyl-lower alkoxy groups are benzyloxy, 2-phenylethoxy, 4-phenylbutoxy and the like. The term "alkanoyloxy group" refers to the residue of an aliphatic carboxylic acid of from 1 to 8 carbon atoms formed by removal of the hydrogen atom from the hydroxyl portion of the carboxyl group. Examples of alkanoyloxy groups are formyloxy, acetoxy, butyryloxy, hexanoyloxy and the like. The term "substituted" as applied to "phenyl" refers to phenyl which is substituted with one or more of the following groups: alkyl, halogen (that is, fluorine, chlorine, bromine or iodine), nitro, cyano, trifluoromethyl and the like. The term aralkyl denoted a radical in which a lower alkyl hydrogen atom is substituted by an aryl group. Exemplary of aralkyl are benzyl, phenylethyl, phenylpropyl and the like. The term aryl denotes an organic radical derived from an aromatic hydrocarbon by the removal of a hydrogen atom. Exemplary of aryl are phenyl and substituted phenyl. The term alkanoyl denotes the residue of an aliphatic carboxylic acid of from 1 to 8 carbon atoms formed by the removal of the hydroxy portion of the carboxyl group. Exemplary of alkanoyl are acetyl, propionyl, butyryl, pentanoyl and the like. The term aralkanoyl denotes an alkanoyl radical in which one hydrogen of the alkyl portion of the molecule has been substituted by aryl. Exemplary of aralkanoyl are phenylacetyl, phenylpropionyl, phenylbutyroyl, phenylpentanoyl and the like. The term aroyl denotes the residue of an aromatic carboxylic acid of from 7 to 20 carbon atoms formed by the removal of the hydroxyl portion of the carboxyl group. Exemplary of aroyl are benzoyl, toloyl and the like. The term acyl denotes the residue of an aliphatic or aromatic carboxylic acid formed by the removal of the hydroxyl portion of the carboxyl group. Exemplary of acyl are aroyl and alkanoyl.

In the formulas represented herein the various substituents are illustrated as joined to the nucleus by one of the following notations. A solid line (—) indicates that a substituent is in the β-orientation, (that is, above the plane of the molecule), a broken line (---) indicates that a substituent is in the α-orientation (that is, below the plane of the molecule), and a wavy line (∿) indicates that the substituent may be in either the α or β orientation or in a mixture of compounds containing substituents in the α and/or β orientation. The Greek letter xi (ξ) in the name of an intermediate indicates that the stereochemistry of the substituent to which it refers is undefined or that the product consists of a mixture of compounds epimeric at the designated position.

As previously mentioned, the compound of formula I is prepared by the reaction of the compound of the formula III, a known compound, with the compound of formula II, a novel compound, the synthesis of which is herein described.

The invention comprises a process for the preparation of a compound of the formula

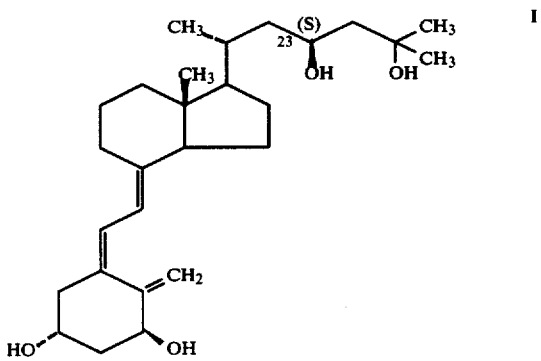

its 23(R) epimer or mixtures thereof which comprises the step of:

(a) reacting the corresponding (S)* or (R)* epimer or mixture thereof, that is, a compound of the formula

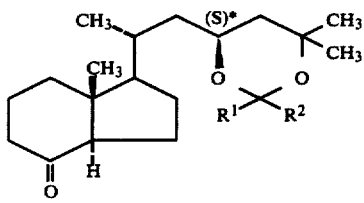

IIa its (R)* epimer or mixture thereof
wherein $R^1$ and $R^2$ each, independently is hydrogen, lower alkyl or aryl, or taken together are lower alkylene of from 3 to 6 carbon atoms, with a compound of the formula

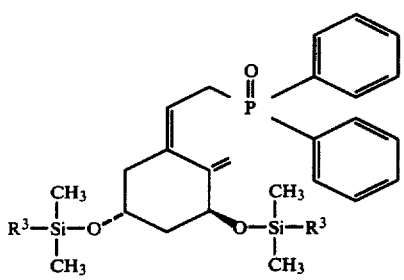

III wherein $R^3$ is lower alkyl or aryl,
to yield the corresponding compound of the formula

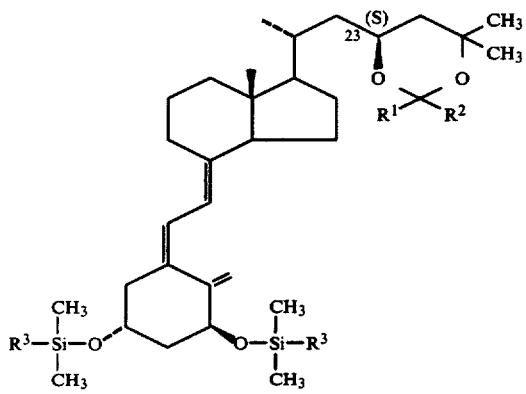

IV its 23(R) epimer or mixtures thereof,
wherein $R^1$, $R^2$ and $R^3$ are as previously described, and (b) removing the protecting groups from the compound of formula IV whereby there is obtained the corresponding compound of formula I, 23(R) epimer or mixtures thereof.

In accordance with the invention, a ketone of the formula II wherein $R^1$ and $R^2$ are as above is reacted with a phosphine oxide of the formula III wherein $R^3$ is as above, which are known compounds or can be prepared according to known procedures, to yield a compound of formula IV wherein $R^1$, $R^2$ and $R^3$ are as above. The reaction is carried out in the presence of a base in a conventional ether solvent under an inert atmosphere at a temperature in the range of from about −80° C. to about −50° C. Exemplary of suitable bases are alkyl lithium compounds and alkali metal dialkyl or disilyl amides. The compound of formula IV can be purified by elution chromatography on silica gel.

The compound of formula IV, its 23(R) epimer or mixtures thereof, is converted to the corresponding compound of formula I by removal of the hydroxyl derivatizing groups by treatment of corresponding compound of formula IV with alcohol or water in the presence of an acid. While any mineral acid or lower alkanoic or sulfonic acid may be used it is preferred to use a cationic ion exchange resin (e.g. AG50W-X4, Bio-Rad Laboratories, Amberlite CG120, Rohm and Haas Co. Amberlyst 15 Rohm and Haas Co., Dowex 50x4, Dow Chemical Co.) as a suspension in a lower alkyl alcohol. The product of the formula I is isolated by filtering off the solid cationic exchange resin and evaporation of the volatiles under reduced pressure.

The compound of formula II, which is the starting material in the process of the invention can be prepared by the process hereinafter, described. An ethylidene compound of the formula

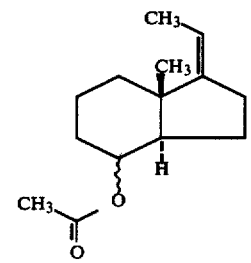

XII is reacted utilizing an ene reaction with a lower alkyl-2-haloacrylate to yield, stereoselectively, with respect to the γ-position of the butanoic acid lower alkyl ester side chain, a compound of the formula

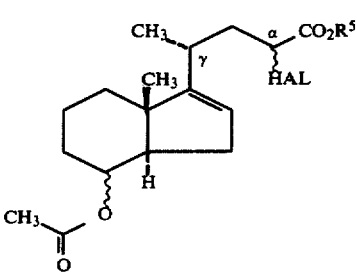

XIII wherein $R^5$ is lower alkyl.

Generally it is preferred to carry out this reaction in the presence of a Lewis acid catalyst, in an inert solvent at temperatures in the range of from about 0° C. to room temperature. On the other hand elevated or reduced temperatures can be utilized.

Exemplary of conventional inert solvents are methylene chloride, carbon tetrachloride, chloroform, aromatic hydrocarbons such as benzene, toluene and the like, and lower aliphatic hydrocarbon solvents such as hexane, heptane, octane and the like. The reaction is carried out a temperatures in the range of from about −20° to 100° C., the particular reaction temperature not being critical. The reaction is catalyzed by Lewis acid catalyst such as lower alkyl aluminum dihalides, and aluminum trihalides in weak base. Exemplary of such catalysts are ethylaluminum dichloride, aluminum tribromide in pyridine or aluminum chloride in pyridine with ethylaluminum dichloride being particularly preferred.

If desired, the mixture of stereoisomers may be separated at this point by elution chromatography which will give about a 1:6 yield of the R to S stereoisomer at the α-position. It is understood that if the R or S stereoisomer is utilized as the starting material in the process which follows the 23(S) or 23(R) compound of formula I, respectively, is obtained. If a mixture is utilized, the corresponding mixture of the 23(S) and 23(R) epimers of formula I is obtained.

If desired, an equilibration procedure may be employed to produce a 1:1 mixture of the R to S isomer starting from the R isomer, S isomer or mixtures thereof. The equilibration is carried out by reaction of a compound of the formula XIII with lithium bromide. The temperature of this reaction is not critical. Generally it is preferred to carry out this reaction at room temperature in a polar solvent such as acetone, dimethylformamide, acetonitrile, dimethylsulfoxide, tetrahydrofuran and the like.

In the next step, the compound of formula XIII is reduced by reaction with a hydride reducing agent in an inert organic solvent so as to yield a compound of the formula

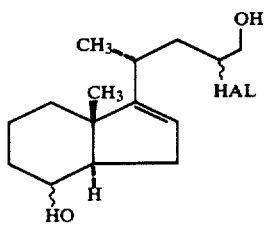

XIV

Exemplary of suitable reducing agents are diisobutylaluminum hydride, and lithium aluminum hydride with diisobutylaluminum hydride being especially preferred. Exemplary of suitable inert organic solvents are lower aliphatic hydrocarbon solvents such as hexane, heptane octane and the like, conventional ether solvents such as diethyl ether and tetrahydrofuran, and aromatic hydrocarbons such as benzene and toluene, or lower alkyl halide solvents such as methylene chloride, chloroform, carbon tetrachloride and the like. The foregoing reaction is carried out a temperatures in the range of about −70° C. to about 80° C. with about 0° C. to about room temperature being preferred.

In the next step, the compound of formula XIV is reacted with a suitable base in a solvent at temperatures in the range of about −70° C. to about 80° C., with about 0° C. to about room temperature being preferred so as to yield a compound of the formula

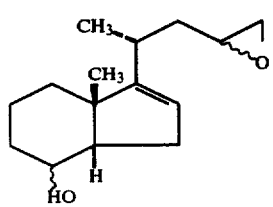

XV

Exemplary of suitable bases are potassium t-butoxide, sodium t-butoxide, potassium isopropoxide, alkali hydroxides such as sodium hydroxide, potassium hydroxide, tri-lower alkylamines and the like. Exemplary of suitable solvents are lower alkyl alcohols such as methanol, ethanol t-butanol, isopropanol, and the like, and conventional ether solvents such as diethyl ether, and tetrahydrofuran.

In the next step, the compound of formula XV is catalytically hydrogenated by reaction with hydrogen in the presence of a hydrogenation catalyst in an inert organic solvent at temperatures in the range of about 0° C. to about 80° C. with room temperature preferred so as to yield a compound of the formula

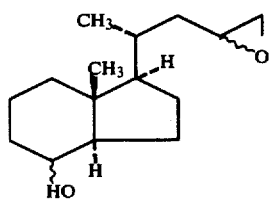

V

Exemplary of suitable hydrogenation catalysts are 5% platinum on carbon, 5–10% palladium on carbon, 5–10% rhodium on carbon, platinum oxide and the like. Exemplary of suitable solvents are lower aliphatic hydrocarbon solvents such as hexane, heptane, octane and the like, lower alkyl alcohols such as methanol, ethanol, propanol and the like, conventional ether solvents such as diethyl ether and tetrahydrofuran, and aromatic hydrocarbon solvents such as benzene and toluene and alkanoic acid alkyl esters such as ethyl formate or ethylacetate.

In the next step, if desired, the compound of formula V is reacted with an silylating agent under an inert atmosphere at temperatures in the range of from about 0° C. to about 80° C. with room temperature preferred so as to yield a compound of the formula

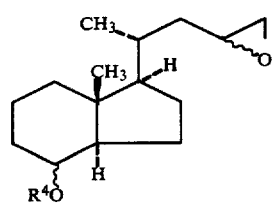

VI wherein $R^4$ is trialkylsilyl, di-loweralkylarylsilyl, lower alkyl diarylsilyl or triarylsilyl. Exemplary of silylating agents are trimethylchlorosilane, triethylchlorosilane, tertiary butyldimethylchlorosilane, chlorodimethylphenylsilane, chlorotriphenylsilane and trimethylsilylimidazole with trimethylsilylimidazole being especially preferred.

In the alternative, the compound of formula V which contains an unprotected hydroxy group may be used as the reagent in the next step.

In the next step, the compounds of formulas V or VI are reacted with a propenylating reagent such as lithium diisopropenyl cuprate, 2-propenyl lithium, or 2-propenylmagnesium bromide so as to yield compounds of the formulas

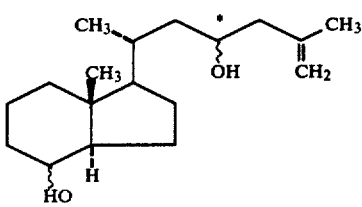

or

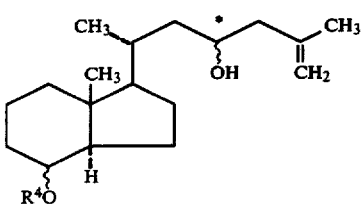

wherein R⁴ is as above.

The compound of formula VII is formed when the compound of formula V is used as the reagent for this step and the compound of formula VIII is formed when the compound of formula VI is used as the reagent for this step. The reaction is carried out in conventional ether solvent such as diethyl ether or tetrahydrofuran or in lower alkyl hydrocarbon/ether cosolvent at temperatures in the range of from about −70° C. to about room temperature with about −15° C. to about −5° C. preferred.

If the compound of formula VIII is prepared, the hydroxy group is deprotected in the next step by reaction with a fluoride ion reagent such as potassium fluoride or tetra-n-butylammonium fluoride, or dilute aqueous acid, mineral acid such as hydrochloric acid, sulfuric acid, perchloric acid and the like in an ether/water cosolvent or aqueous lower alcoholic solvent so as to yield the compound of formula VII.

If desired a mixture of the R* and S* diastereomers of VII may be separated by elution chromatography on silica gel.

In the next step, the compound of formula VII is reacted with an epoxidizing agent at temperatures in the range of from about −70° C. to about 80° C. with about 0° C. to about room temperature preferred so as to yield a compound of the formula

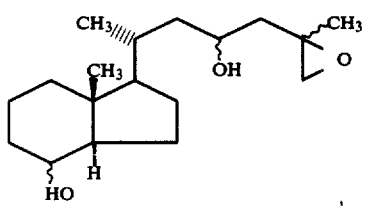

Exemplary of suitable epoxidizing agents are M-chloroperbenzoic acid, peracetic acid, t-butylhydroperoxide in the presence of a transition metal catalyst such as molybdenum hexacarbonyl with M-chloroperbenzoic acid preferred.

In the next step the compound of formula IX is converted to the compound of formula

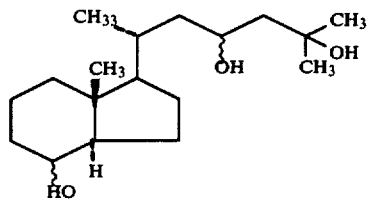

by treating the compound of formula IX with a reducing agent. Any conventional reducing agent which will reduce an epoxide to an alcohol may be utilized in carrying out this reaction. Among the preferred reducing agents are hydride reagents such as lithium aluminum hydride, sodium borohydride, diisobutylaluminum hydride, lithium tri-t-butoxy aluminum hydride.

In the next step the compound of formula X is converted to the compound of formula wherein R¹ and R² are as above
by treating the compound of formula XI with conventional reagents capable of converting a 1,3 diol to the corresponding 1,3-dioxane derivative.

Among the preferred reagents for this conversion are ketones and aldehydes in the presence of an acid catalyst and a dehydrating agent, vinyl ethers in the presence of an acid catalyst. Exemplary of acid catalysts are toluenesulfonic acid monohydrate, oxalic acid, trifluoroacetic acid, mineral acid, for example hydrochloric acid, and cationic ion exchange resins. Exemplary of dehydrating agents are anhydrous cupric sulfate, anhydrous magnesium sulfate, and molecular sieves. Exemplary of suitable vinyl ether moieties are methyl or ethyl vinyl ether, methyl cyclohexenyl ether, methyl 2-propenyl ether and the like. Exemplary of suitable ketones are acetone, cyclohexanone, and the like. Exemplary of suitable aldehydes are formaldehyde, acetaldehyde, benzaldehyde and the like. Solvent is not necessary for this conversion although if desired conventional inert solvents may be used.

Suitable organic solvents are hexane, heptane, octane benzene, toluene, methylene chloride, ether, ethyl acetate and the like.

In the next step the compound of formula XI is converted to the compound of formula

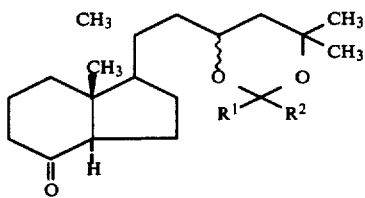

wherein R¹ and R² are as above, by treatment with an oxidizing agent. Suitable oxidizing agents are chromium based compounds among which are pyridium chlorochromate, 2,3-bipyridinium chlorochromate, pyridine-chromium trioxide and the like, and activated dimethylsulfoxide. The synthetic application of activated dimethylsulfoxide has been reviewed extensively by A. J. Mancuso and D. Swern, Synthesis, 165 (1981).

The 23(R) epimer, that is, the $1\alpha,23(R),25$-trihydroxycholecalciferol, is characterized by the formula

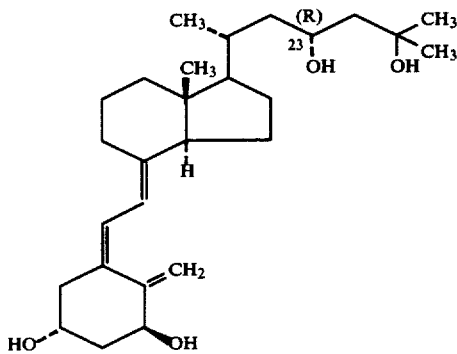

The compounds of formula I, its 23(R) epimer and mixtures thereof, can be administered in dosages that are in the range of about 5-10 micrograms per day for the treatment of such disease states as osteodystrophy, steroid induced osteopenia, hypoparathyroidism, hypophosphatemic rickets and hypophosphatemic osteomalacia which are characterized by lower than normal levels of endogenously produced $1\alpha,25$-dihydroxycholecalciferol.

The compounds of formula I, its 23(R) epimer or mixtures thereof, can also be administered in dosages that are in the range of from about 5-20 micrograms per day for the treatment of osteoporosis. A preferred dosage for the treatment of the above disease states is about 10 micrograms per day. The compound of formula I can be administered orally, subcutaneously, intramuscularly, intravenously, or intraperitoneally.

The useful activity of the compound of formula I, its 23(R) epimer or mixtures thereof can be demonstrated utilizing, for instance, the test procedure which follows:

In vitro Cytosol Receptor Binding Assay

The test compound and tritium labelled calcitriol, both in isopropanol, were incubated with chick intestinal cytosol binding protein for 60 minutes at room temperature. Bound $^3$H-calcitriol was separated from unbound $^3$H-calcitriol using polyethylene glycol. The extent of binding was determined by measuring the decrease in binding of $^3$H-calcitriol at each concentration of test compound compared with binding in the absence of test compound. The binding ratio, used to compare activities of compounds, was calculated from the concentration of nonradioactive test compound compared to the concentration of calcitriol which decreased the binding of $^3$H-calcitriol to the cytosol binding protein by 50%.

The cytosol binding protein used in the test was obtained from rachitic chicks maintained on a vitamin D deficient diet for 8 weeks. The intestinal mucosa was removed from the duodenal loop, homogenized and centrifuged at 105,000 g. The obtained supernatant (cytosol) contained the intestinal receptors for $1\alpha,25$-dihydroxyvitamin $D_3$ and was used in the binding assay.

The binding of test compounds relative to $1\alpha,25$-dihydroxyvitamin $D_3$ is shown in Table I.

TABLE I

| Compound | Ratio Relative[1] to $1\alpha,25$-$(OH)_2$—$D_3$ Binding |
| --- | --- |
| $1\alpha,25$-$(OH)_2$—$D_3$ | 1 |
| $1\alpha,23(S),25$-$(OH)_3$—$D_3$ | 90 |
| $1\alpha,23(R),25$-$(OH)_3$—$D_3$ | 87 |

[1]Calculated from the ratio of the concentration of analog to the concentration of $1\alpha,25$-$(OH)_2$—$D_3$ which decreased by 50% the binding of H—$1\alpha,25$-$(OH)_2$—$D_3$ to the cytosol binding protein.

The compound of formula I, its 23(R) epimer or mixtures thereof, can be formulated in compositions such as tablets, capsules, and the like, or elixirs for oral administration, or in sterile solutions or suspensions for parenteral administration. About 5-20 micrograms of the compound of formula I, its 23(R) epimer or mixtures thereof, can be compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and in flavoring such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

$1\alpha,23(S),25$-trihydroxycholecalciferol has shown activity in the antirachitogenic activity test in chicks.

The examples which follow further illustrate the disclosure. All temperatures are in degrees Centigrade unless otherwise stated.

EXAMPLE 1

Preparation of [3aS-[3a$\alpha$3(R*,R*),7$\beta$,7$\beta$]-7-(Acetyloxy)-$\alpha$-bromo-3a,4,5,6,7,7a-hexahydro-$\gamma$,3a-dimethyl-1H-indene-3-butanoic acid methyl ester To a solution of 6.8 g of (—)[3aR[(Z);3a alpha, 4 alpha, 7 beta]-1-ethylidene octahydro-7a-methyl-1H-4-indenol acetate (94.4% isomerically pure by GC on a 1M 3% OV-17 column, 80°-260° C. at a 2° C./minute gradient), 200 mL of methylene chloride dried over 4 Å sieves prior to use and 56 mL of a 0.827M solution of methyl-α-bromoacrylate in methylene chloride under an atmosphere of dry argon and with cooling in an ice bath is added dropwise over fifteen minutes 51.9 mL of a 1.49M solution of ethylaluminum dichloride in hexane. The cooling bath was removed and the mixture was stirred at room temperature for 25 hours and then poured into ice containing 250 mL of 10% (w/v) of aqueous potassium sodium tartrate then extracted 3×250 mL of methylene chloride. The combined extracts which contained an emulsion were filtered through celite and then washed successively with water, brine and dried over anhydrous sodium sulfate. Filtration and removal of solvent in vacuo produced 16 g of crude product. Chromatography on 150 g of silica gel (40–63μ) eluting with hexane/ethyl acetate (15:1) gave 8.5 g of a 13:87 mixture (25 cm Porasil column, heptane/ethyl acetate, 9:1, RI detector) of [3aS-[3aα3(R*,R*), 7β,7aβ]-7-(acetyloxy)-α-bromo-3a,4,5,6,7,7a-hexahydro-γ,3a-dimethyl-1H-indene-3-butanoic acid methyl ester and its alphaS isomer. The mixture was stirred at room temperature with 9.53 g (0.110 mol) of anhydrous lithium bromide in 300 mL of reagent grade acetone overnight. Solvent was removed in vacuo, 200 mL of water added to the residue and the mixture extracted 2×100 mL of methylene chloride. The combined extracts were washed successively with water, brine and dried over anhydrous sodium sulfate. Filtration followed by removal of solvent in vacuo gave 8.2 g of product as a 1:1 mixture of 3aS-[3aα3(R*,R*), 7β,7aβ]-7-(Acetyloxy)-α-bromo-3a,4,5,6,7,7a-hexahydro-γ,3a-dimethyl-1H-indene-3-butanoic acid methyl ester and its alphaS isomer. Separation of the two isomers was achieved by medium pressure liquid chromatography of 1–2 g portions through a 2.5×100 cm Altex column packed with 40–63μ silica gel eluting with hexane/ethyl acetate (7:1). The more polar alphaS isomer was resubmitted to the lithium bromide/acetone equilibration-separation sequence described above three more times to give a total yield of 7.1 g (63%) of 3aS-[3a alpha, 3(R*,R*),7beta, 7a beta]-7-(Acetyloxy)-alpha-bromo-3a,4,5,6,7,7a-hexahydro-gamma,3a-dimethyl-1H-indene-3-butanoic acid methyl ester. The analytical sample was recrystallized from hexane/ether. MP 62° C.; $[\alpha]_D^{25}+41.14°$ (c 1.0063, CHCl₃). Calcd. for $C_{18}H_{27}BrO_4$: C, 55.82; H, 7.03; Br, 20.63 Found: C, 56.06; H, 7.10; Br, 20.44.

In a separate experiment, the analytical sample of the other isomer, 3aS-[3a alpha, 3(R*,S*), 7 beta, 7a beta]-7-(Acetyloxy)-alpha-bromo-3a,4,5,6,7,7a-hexahydro-gamma,3a-dimethyl-1H-indene-3-butanoic acid methyl ester was obtained as an oil by eliminating the lithium bromide/acetone equilibration step. $[\alpha]_D^{25}-40.91°$ (c 0.9925, CHCl₃). Calculated for $C_{18}H_{27}BrO_4$: C,55.82; H, 7.03; Br, 20.63. Found: C, 55.50; H, 6.92; Br, 20.65.

EXAMPLE 2

Preparation of 3aS-[3a alpha,3(R*,R*), 7beta, 7a beta]-3-(3-Bromo-4-hydroxy-1-methylbutyl)-hexahydro-3a-methyl-1H-inden-7-ol To a solution of 92.2 mL of 20% diisobutylaluminum hydride in hexane and 90 mL of tetrahydrofuran (freshly distilled from sodium/benzophenone) at 0° C. is added a solution of 6.7 g of 3aS-[3a alpha, 3(R*,R*), 7beta, 7a beta]-7-(Acetyloxy)-alpha-bromo-3a,4,5,6,7,7a-hexahydro-gamma, 3a-dimethyl-1H-indene-3-butanoic acid methyl ester in 80 mL of dry tetrahydrofuran over fifteen minutes. The cooling bath was removed and the mixture allowed to stir at room temperature for 45 minutes. The mixture was then poured into 750 mL of ice water and acidified with 1N hydrochloric acid, then extracted 3×250 mL of ethyl acetate. The extracts were washed with water and brine until neutral then dried over anhydrous sodium sulfate. After filtration and evaporation of solvent, the residue was chromatographed (medium pressure LC) on silica gel eluting with hexane/ethyl acetate (2:1) to give 5.0 g (91%) of 3aS-[3a alpha,3(R*,R*),7beta, 7a beta]-3-(3-Bromo-4-hydroxy-1-methylbutyl)hexahydro-3a-methyl-1H-inden-7-ol as an oil. $[\alpha]_D^{25}+19.88°$ (c 0.5532, CHCl₃); Calculated for $C_{15}H_{25}BrO_2$: C, 56.79; H, 7.94; Br, 25.19. Found: C, 56.61; H, 7.93; Br, 25.27.

EXAMPLE 3

Preparation of [3aS-[3a alpha,3(R*,S*),7beta, 7a beta]]-Hexahydro-3a-methyl-3-(1-methyl-2-oxiranylethyl)-1H-inden-7-ol To a solution of 4.6 g of [3aS-[3a alpha, 3(R*,R*), 7beta, 7a beta]]-3-(3-Bromo-4-hydroxy-1-methylbutyl)-hexahydro-3a-methyl-1H-inden-7-ol in 145 mL of dry t-butanol under an argon atmosphere and at room temperature is added 2.1 g of potassium t-butoxide. After stirring 50 minutes the mixture was cooled in an ice bath and 10 mL of saturated aqueous sodium dihydrogen phosphate was added. The mixture was stirred 10 minutes then poured into 500 mL of ice water and extracted 3×200 mL of methylene chloride. The combined extracts were washed successively with water, brine then dried over anhydrous sodium sulfate. Filtration and evaporation of solvent in vacuo gave 3.5 g of crude product. Medium pressure liquid chromatography eluting with hexane/ethyl acetate (1:1) gave 2.9 g (84%) of [3aS[3a alpha,3(R*,S*),7beta, 7a beta]]-Hexahydro-3a-methyl-3-(1-methyl-2-oxiranylethyl)-1H-inden-7-ol. The analytical sample was crystallized from hexane/ethyl acetate. MP 62.5°–63° C.; $[\alpha]_D^{25}-31.26°$ (c 1.0300, CHCl₃). Calculated for $C_{15}H_{24}O_2$: C, 76.23; H, 10.24. Found: C 75.95; H, 10.01.

EXAMPLE 4

Preparation of [1R-[1alpha(R*,S*), 3a beta, 4beta,7a alpha]]-Octahydro-7a-methyl-1-(1-methyl-2-oxiranylethyl)-1H-inden-4-ol A mixture of 2.9 g of [3aS-[3a alpha, 3(R*,S*),7beta, 7a beta]]-Hexahydro-3a-methyl-3-(1-methyl-2-oxiranylethyl)-1H-inden-7-ol, 0.29 g of 5% platinum on carbon catalyst and 125 mL of ethyl acetate was stirred at room temperature under an atmosphere of hydrogen. When hydrogen uptake ceased (3 hours), the mixture was filtered and solvent removed in vacuo. The residue was chromatographed (2.5×100 cm Altex column, 40–60 silica gel) eluting with hexane/ethyl acetate (1:1) to give 2.1 g (72%) of [1R-[1alpha(R*,S*),3a beta, 4beta, 7a alpha]]-Octahydro-7a -methyl-1-(1-methyl-2-oxiranylethyl)-1H-inden-4-ol as an oil. $[\alpha]_D^{25}-3.18°$ (c 1.0992, CHCl₃). Calculated for $C_{15}H_{26}O_2$: C, 75.48; H, 10.99. Found: C, 75.45; H, 10.69.

EXAMPLE 5

Preparation of [1R-[1alpha(R*,S*),3a beta, 4beta, 7a alpha]]-Octahydro-7a-methyl-1-(1methyl-2-oxiranylethyl)-1H-inden-4-ol trimethylsilyl ether To a solution of 1.4 g of [1R-[1alpha(R*,S*), 3a beta, 4beta, 7a alpha]]-Octahydro-7a-methyl-1-(1-methyl-2- oxiranylethyl)-1H-inden-4-ol and 40 mL of ethyl acetate is added 1.64 g of trimethylsilylimidazole. The mixture was stirred under a dry argon atmosphere at room temperature for 20 minutes then poured into 100 mL of cold water and extracted 3×25 mL of heptane/ethyl acetate (1:1). The extracts were washed with 3×50 Ml of water and dried over anhydrous sodium sulfate. The mixture was filtered and solvent removed in vacuo. Chromatography on silica gel (2.5×100 cm Altex column, 40–60μ silica gel) eluting with hexane/ethyl acetate (6:1) gave 1.81 g (99%) of [1R-[1alpha(R*,S*),3a beta, 4beta, 7a alpha]]-Octahydro-7a-methyl-1-(1-methyl-2-oxiranylethyl)-1H-inden-4-ol trimethylsilyl ether. This material which contained traces of starting material and slowly reverted to starting material on standing was used with no further purification.

EXAMPLE 6

Preparation of [1R-[1alpha(R*,S*), 3a beta, 4 beta, 7a alpha]]-Octahydro-1-(3-hydroxy-1,5-dimethyl-5-hexenyl)-7a-methyl-1H-inden-4-ol To a solution of 1.1 g of freshly distilled 2-bromopropene and 15 mL of anhydrous diethyl ether at −78° C. under an argon atmosphere is added 5.65 mL of 1.6M t-butyllithium in pentane. After stirring 1 hour, a clear solution of tributylphosphine/cuprous iodide in ether (prepared by the of tributylphosphine to a stirred mixture of 0.661 g of cuprous iodide and 15 mL of anhydrous diethyl ether followed by stirring at room temperature for 1 hour) was added dropwise to the mixture. After stirring five minutes, 0.292 g of [1R-[1alpha(R*,S*), 3a beta, 4 beta,7a alpha]]-octahydro-7a-methyl-1-(1-methyl-2-oxiranylethyl)-1H-inden-4-ol trimethyl silyl ether in 15 mL of anhydrous diethyl was added dropwise to the brownish yellow solution. The mixture was stirred five minutes then the cooling bath was replaced with a methanol/water/ice bath (−15° to −10° C.). After stirring at that temperature for 2½ hours, 15 mL of saturated aqueous sodium dihydrogen phosphate solution was added and stirred five minutes. The mixture was then poured into 50 mL of water and extracted 3×30 mL of diethyl ether. The combined extracts were washed successively with water, brine and dried over anhydrous sodium sulfate. Filtration and evaporation of solvent gave the crude product as an oil. This was first flash chromatographed on 75 g of silica gel (40–60μ) eluting with hexane/ethyl acetate (10:1) then medium pressure LC (Altex 2.5×100 cm column, 40–60μ silica gel) eluting with hexane/ethyl acetate (10:1) to give 0.253 g (77%) of impure [1R-[1alpha(R*,S*),3a beta, 4beta,7a alpha]]-octahydro-1-(3-hydroxy-1,5-dimethyl-5-hexenyl)-7a-methyl-1H-inden-4-ol mono trimethylsilyl ether. With no further purification this was stirred with 10 mL of tetrahydrofuran, 4 mL of methanol, 1 mL of water, and 0.3 g of tetra-n-butylammonium fluoride until the reaction was judged completed by thin layer chromatography. Approximately half of the solvent was removed under water aspirator vacuum. The mixture was poured into 30 mL of water and extracted 3×20 mL of diethyl ether/hexane (1:1) and dried over anhydrous sodium sulfate. Filtration and evaporation of solvent in vacuo gave 0.191 g of product. This was combined with product obtained from a similar experiment using 0.20 g of starting material and chromatographed on silica gel (2.5×100 cm Altex column, 40–63μ silica gel) eluting with hexane/ethyl acetate (2:1) to give a total of 0.320 g (72% yield based on 0.492 g total of starting material used in the two reactions) [1R-[1 alpha (R*,S*), 3a beta, 4 beta, 7a alpha]]-octahydro-1-(3-hydroxy-1,5-dimethyl-5-hexenyl)-7a-methyl-1H-inden-4-ol. The analytical sample was recrystallized from ethyl acetate/hexane. MP 98°-98.5° C. $[\alpha]_D^{25}+19.31°$ (c 0.9940, CHCl$_3$); Calculated for $C_{18}H_{32}O_2$: C, 77.08; H, 11.50. Found: c, 77.21; H, 11.29.

EXAMPLE 7

Preparation of 1R-[1alpha(R*-,S*-,R*-),3a beta, 4beta,7a alpha]-octahydro-1-[3-hydroxy-1-methyl-4-(1-methyloxiranyl)butyl]-7a-methyl-1H-inden-4-ol and 1R-[1alpha(R*-,S*-,S*-), 3a beta, 4beta, 7a alpha]-octahydro-1-[3-hydroxy-1-methyl-4-(1-methyloxiranyl)-butyl]-7a-methyl-1H-inden-4-ol To a solution of 0.90 g of [1R-[1alpha(R*,S*),3a beta, 4 beta, 7a alpha]]-octahydro-1-(3-hydroxy-1,5-dimethyl-5-hexenyl)-7a-methyl-1H-inden-4-ol in 10 mL of methylene chloride dried over 4 Å sieves) cooled to 0° C. is added 0.090 g of 85% m-chloroperbenzoic acid. The cooling bath was removed and mixture stirred one hour then an additional 0.045 g of 85% m-chloroperbenzoic acid added. After 15 minutes the mixture was poured into 50 mL of water and extracted 1×50 mL of methylene chloride. The extract was washed 2×25 mL of 10% aqueous sodium sulfite, 2×25 mL of ice cold 1N potassium carbonate then washed with water until neutral followed by a brine wash and then dried over anhydrous sodium sulfate. Filtration and evaporation of solvent gave 1R-[1 alpha (R*, S*, R*), 3a beta, 4 beta, 7a alpha]-octahydro-1-[3-hydroxy-1-methyl-4-(1-methyloxiranyl)butyl]-7a-methyl-1H-inden-4-ol and 1R-[1alpha-(R*,S*,S*),3a beta, 4beta, 7a alpha]-octahydro-1-[3-hydroxy-1-methyl-4-(1-methyloxiranyl)butyl]-7a-methyl-1H-inden-4-ol as a 1:1 mixture [LC analysis on 25 cm Porasil column, heptane/ethyl acetate (35:65)]. This material was used directly in the next step with no further purification.

EXAMPLE 8

Preparation of [1R-[1alpha(R*,S*),3a beta, 4beta,7a alpha]]-Octahydro-4-hydroxy-7a-methyl-1H-inden-1-yl)-1,6-dimethyl-2,4-hexanediol To a mixture of 0.010 g of lithium aluminum hydride and 10 mL of dry tetrahydrofuran at 0° C. is added a solution of 0.080 g of epoxides obtained from example 7 in 5 mL of dry tetrahydrofuran. After stirring for one hour under an argon atmosphere, the mixture was quenched by addition of 15 mL of ethyl acetate followed by 5 mL of saturated aqueous sodium sulfate solution. After stirring five minutes, the mixture was acidified by addition of 0.5N hydrochloric acid then extracted 4×25 mL of ethyl acetate. The combined extracts were washed with water until neutral followed by a brine wash and drying over anhydrous sodium sulfate. After filtration and removal of solvent, 0.081 g of [1R-[1alpha(R*,S*),3a beta, 4beta,7a alpha]]-octahydro-4-hydroxy-7a -methyl-1H-inden-1-yl)-1,6-dimethyl-2,4-hexanediol was of sufficient purity for use in the next step without further purification. An analytical sample was obtained by crystallization from hexane/ethyl acetate. MP 140°-141° C.; $[\alpha]_D^{25}+25.44°$ (C 0.2988, dioxane). Calculated for $C_{18}H_{34}O_3$: C, 72.44; H, 11.48. Found: C, 72.09; H, 11.28.

EXAMPLE 9

Preparation of 1R-[1alpha(R*,S*),3a beta, 4beta,7a alpha]-octahydro-1-[1-methyl-2-(2,2,4,4-tetramethyl-1,3-dioxan-6-yl)ethyl]-7a-methyl-1H-inden-4-ol A mixture of 0.45 g of [1R-[1alpha(R*,S*), 3a beta, 4beta, 7a alpha]]-octahydro-4-hydroxy-7a-methyl-1H-inden-1-yl)-1,6-dimethyl-2,4-hexanediol, 30 mL of 2,2-dimethoxypropane and 0.050 g of p-toluenesulfonic acid monohydrate was stirred under an argon atmosphere at room temperature for 4 hours then quenched by addition of 3 mL of saturated aqueous sodium bicarbonate solution. Solvent was removed under water aspirator vacuum. 25 mL of water was added to the residue and extracted 2×25 mL of ethyl acetate. The combined extracts were washed successively with water, brine and dried over anhydrous sodium sulfate. Filtration and evaporation of solvent in vacuo gave the crude product as an amber oil. This was chromatographed on silica gel (2×5×100 cm Altex column, 40–63μ silica gel) eluting with hexane/ethyl acetate/methylene chloride (5:1:1) to give 0.36 g (71% yield) of 1R-[1alpha(R*,S*),3a beta, 4beta,7a alpha]-octahydro-1-[1-methyl-2-(2,2,4,4-tetramethyl-1,3-dioxan-4-yl)ethyl]-7a-methyl-1H-inden-4-ol as a solid. MP 78°–80° C.

EXAMPLE 10

Preparation of 1R-[1alpha(R*,S*),3a beta, 4beta, 7a alpha]-octahydro-1-[1-methyl-2-(2,2,4,4-tetramethyl-1,3-dioxan-6-yl)ethyl]-7a-methyl-1H-inden-4-one A solution of 0.101 g of 1R-[1alpha(R*,S*),3a beta, 4beta, 7a alpha]-octahydro-1-[1-methyl-2-(2,2,4,4-tetramethyl-1,3-dioxan-6-yl)ethyl]-7a-methyl-1H-inden-4-ol in 6 mL of dry methylene chloride was treated with 0.170 g of anhydrous sodium acetate and 0.345 g of 2,2'-bipyridinium chlorochromate and the mixture stirred at room temperature for 2 hours. After this time, additional 0.150 g of 2,2'-bipyridinium chlorochromate was added and the stirring continued for 1 more hour. Water was then added to the reaction mixture which was extracted with 3×50 mL of ether. The combined organic phases were washed with water, dried and evaporated. The crude residue obtained was purified by chromatography on silica, eluting with hexane/ethyl acetate (2:1) to give 0.090 g (90% yield) of pure 1R-[1alpha(R*,S*),3a beta, 4beta, 7a alpha]-octahydro-1-[1-methyl-2-(2,2,4,4-tetramethyl-1,3-dioxan-6-yl)ethyl]-7a-methyl-1H-inden-4-one.

EXAMPLE 11

Preparation of (1 alpha, 3 beta, 5Z, 7E,23S)-9,10-Secocholesta-4,7,10(9)-triene-1,3-bis[(1,1-dimethylethyl)-dimethylsilyloxy]-23,25-diol-(1-methylethylidene)-cyclic acetal A solution of 0.280 g of [3S-3alpha, 5beta, Z)]-2-[2-methylene-3,5-bis-[1,1-dimethylethyl)dimethylsilyloxy]cyclohexylidene]ethyldiphenyl phosphine oxide in 6 mL of dry tetrahydrofuran was cooled at −78° C. and treated dropwise under argon, with 0.275 ml of a 1.7M solution of n-butyllithium in hexane. After stirring for 5 minutes a solution of 0.091 g of 1R-[1alpha(R*,S*)-,3abeta,4beta,7a alpha]-octahydro-1-[1-methyl-2-(2,2,4,4-tetramethyl-1,3-dioxane-6-yl)ethyl]-7a-methyl-1H-inden-4-on in 1.5 mL of tetrahydrofuran was slowly added and the mixture stirred at −78° C. for 2 hours. It was then treated with 2 mL of a 1:1 mixture of 1N sodium bicarbonate and 1N potassium sodium tartrate, allowed to cool to room temperature, diluted with water and extracted with 3×50 mL of ethyl acetate. The combined organic extracts were washed with brine, dried and evaporated. The residue was purified by chromatography on silica, eluting with hexane/ethyl acetate (5:1) to give 0.172 g of the product (1 alpha, 3 beta, 5Z, 7E, 23S)-9,10-secocholesta-5,7,10(9)-triene-1,3-bis[(1,1-dimethylethyl)-dimethylsilyloxy]-23,25-diol-(1-methylethylidene)-cyclic acetal as a thick colorless oil. This was used directly in the next step.

EXAMPLE 12

Preparation of (1 alpha, 3 beta, 5Z, 7E, 23S)-9,10-Secocholesta-5,7,10(19)-triene-1,3,23,25-tetrol. (Syn. 1 alpha,23S,25-Trihydroxycholecalciferol)

The product from Example 11 0.172 g was dissolved in 9 mL of dry methanol, treated with 3 g of a cation exchange resin and stirred overnight. After filtration and washing of the resin with 20 mL of methanol, the solvent was evaporated in vacuo and the residue dissolved in 80 mL of ethyl acetate and washed with 2×20 mL of 2N sodium bicarbonate solution followed by 3×20 mL of brine. The residue obtained after evaporation of the solvent was purified by chromatography on silica, eluting with ethyl acetate, to give 0.106 g (90% yield) of pure 1 alpha, 23S,25-trihydroxycholecalciferol as a white amorphous powder. $[\alpha]_D^{25} + 47.3°$ (c 0.2, EtOH). Calculated for $C_{27}H_{44}O_4$: C, 74.96; H, 10.25. Found: C, 74.88; H, 9.95.

EXAMPLE 13

Preparation of [3aS-[3a alpha,3(R*,S*), 7 beta, 7a beta]-3-(3-Bromo-4-hydroxy-1-methylbutyl)-hexahydro-3a-methyl-1H-inden-7-ol Following the procedure of example 2, [3aS-[3a alpha, 3(R*,S*), 7 beta, 7a beta]-7-(acetyloxy)-alpha-bromo-3a,4,5,6,7,7a-hexahydro-gamma,3a-dimethyl-1H-indene-3-butanoic acid methyl ester was converted to [2aS-[2a alpha, 3(R*,S*), 7 beta, 7a beta]-3-(3-bromo-4-hydroxy-1-methylbutyl)hexahydro-3a-methyl-1H-inden-7-ol, mp 153°–154° C., $[\alpha]_D^{25} - 69.13°$ (C, 0.3966, CHCl$_3$).

EXAMPLE 14

Preparation of [3aS[3a alpha, 3(R*,R*), 7 beta, 7a beta]]-Hexahydro-3a-methyl-3-(1-methyl-2-oxiranylethyl)-1H-inden-7-ol Following the procedure of example 3, [3aS-[3a alpha, 3(R*,S*), 7 beta, 7a beta]]-3-(3-bromo-4-hydroxy-1-methylbutyl)hexahydro-3a-methyl-1H-inden-7-ol was converted to [3aS-[2a alpha, 3(R*,R*), 7 beta, 7a beta]]-hexahydro-3a-methyl-3-(1-methyl-2-oxiranylethyl)-1H-inden-7-ol, an oil distilled bulb to bulb 75° C. 0.075 mmHg, $[\alpha]_D^{25} - 16.39°$ (C, 0.3966,CHCl$_3$).

EXAMPLE 15

Preparation of [1R-[1 alpha(R*,R*), 3a beta, 4 beta, 7a alpha]]-Octahydro-7a-methyl-1-(1-methyl-2-oxiranylethyl)-1H-inden-4-ol Following the procedure of example 4, [3aS-[3a alpha, 3(R*,R*), 7 beta, 7a beta]]-hexahydro-3a-methyl-3-(1-methyl-2-oxiranylethyl)-1H-inden-7-ol was converted to [1R-[1 alpha (R*,R*), 3a beta, 4 beta, 7a alpha]]-octahydro-7a-methyl-1-(1-methyl-2-oxiranylethyl)-1H-inden-4-ol, an oil which was distilled bulb to bulb @75° C.@0.10 mmHg, [α]$_D^{25}$ +11.11° (C, 0.4952, CHCl$_3$).

EXAMPLE 16

Preparation of [1R-[1 alpha (R*,R*), 3a beta, 4 beta, 7a alpha]]-Octahydro-7a-methyl-1-(1-methyl-2-oxiranylethyl)-1H-inden-4-ol trimethylsilyl ether Following procedure of example 5, [1R-[1 alpha (R*,R*), 3a beta, 4 beta, 7a alpha]]-octahydro-7a-methyl-1-(1-methyl-2-oxiranylethyl)-1H-inden-4-ol and was converted to [1R-[1 alpha (R*,R*), 3a beta, 4 beta, 7a alpha]]-octahydro-7a-methyl-1-(1-methyl-2-oxiranylethyl)-1H-inden-4-ol trimethylsilyl ether, an oil which was distilled bulb to bulb at 80° C.@0.10 mmHg, [α]$_D^{25}$ +14.24° (C, 0.8780, CHCl$_3$).

EXAMPLE 17

Preparation of [1R-[1 alpha(R*,R*), 3a beta, 4 beta, 7a alpha]]-Octahydro-1-(3-hydroxy-1,5-dimethyl-5-hexenyl)-7a-methyl-1H-inden-4-ol Following the procedure of example 6, [1R-[1 alpha (R*,R*), 3a beta, 4 beta, 7a alpha]]-octahydro-7a-methyl-1-(1-methyl-2-oxiranylethyl)-1H-inden-4-ol trimethylsilyl ether was converted to [1R-[1 alpha(R*,R*), 7a beta, 4 beta, 7a alpha]]-octahydro-1-(3-hydroxy-1,5-dimethyl-5-hexenyl)-7a-methyl-1H-inden-4-ol.

EXAMPLE 18

Preparation of 1R-[1 alpha(R*,R*,R*),3a beta, 4 beta, 7a alpha]-Octahydro-1-[3-hydroxy-1-methyl-4-(1-methyloxiranyl)butyl]-7a-methyl-1H-inden-4-ol and 1R-[1 alpha-(R*,R*,S*), 3a beta, 4 beta, 7a alpha]-octahydro-1-[3-hydroxy-1-methyl-4-(1-methyloxiranyl)butyl]-7a-methyl-1H-inden-4-ol Following the procedure of example 7, [1R-[1 alpha(R*,R*), 3a beta, 4 beta, 7a alpha]]-octahydro-1-(3-hydroxy-1,5-dimethyl-5-hexenyl)-7a-methyl-1H-inden-4-ol was converted to 1R-[1 alpha (R*,R*,R*), 3a beta, 4 beta, 7a alpha]-octahydro-1-[3-hydroxy-1-methyl-4-(1-methyloxiranyl)butyl]-7a-methyl-1H-inden-4-ol and 1R-[1 alpha (R*,R*,S*), 3a beta, 4 beta, 7a alpha-octahydro-1-[3-hydroxy-1-methyl-4-(1-methyloxiranyl)butyl]-7a-methyl-1H-inden-4-ol.

EXAMPLE 19

Preparation of [1R-[1 alpha(R*,R*), 3a beta, 4 beta, 7a alpha]]-Octahydro-4-hydroxy-7a-methyl-1H-inden-1-yl)-1,6-dimethyl-2,4-hexanediol Following the procedure of example 8, 1R-[1 alpha (R*,R*,R*), 3a beta, 4 beta, 7a alpha]-octahydro-1-[3-hydroxy-1-methyl-4-(1-methyloxiranyl)butyl]-7a-methyl-1H-inden-4-ol and 1R-[1 alpha (R*,R*,S*), 3a beta, 4 beta, 7a alpha-octahydro-1-[3-hydroxy-1-methyl-4-(1-methyloxiranyl)butyl]-7a-methyl-1H-inden-4-ol was converted to [1R-[1 alpha (R*,R*), 3a beta, 4 beta, 7a alpha]]-octahydro-4-hydroxy-7a-methyl-iH-inden-1-yl)-1,6-dimethyl-2,4-hexanediol.

EXAMPLE 20

Preparation of 1R-[1 alpha(R*,R*), 3a beta, 4 beta, 7a alpha]-Octahydro-1-[1-methyl-2-(2,2,4,4-tetramethyl-1,3-dioxan-4-yl)ethyl]-7a-methyl-1H-inden-4-ol Following the procedure of example 9, [1R-[1 alpha (R*,R*), 3a beta, 4 beta, 7a alpha]]-octahydro-4-hydroxy-7a-methyl-1H-inden-1-yl)-1,6-dimethyl-2,4-hexanediol was converted to 1R-[1 alpha (R*,R*), 3a beta, 4 beta, 7a alpha]-octahydro-1-[1-methyl-2-(2,2,4,4-tetramethyl-1,3-dioxan-4-yl)ethyl]-7a-methyl-1H-inden-4-ol, [α]$_D^{25}$ +55.98° (C, 0.6967, CHCl$_3$).

EXAMPLE 21

Preparation of 1R-[1 alpha(R*,R*), 3a beta, 4 beta, 7a alpha]-Octahydro-1-[1-methyl-2-(2,2,4,4-tetramethyl-1,3-dioxan-6-yl)ethyl]-7a-methyl-1H-inden-4-one Following the procedure of example 10, 1R-[1 alpha (R*,R*), 3a beta, 4 beta, 7a alpha]-octahydro-1-[1-methyl-2-(2,2,4,4-tetramethyl-1,3-dioxan-6-yl)ethyl]-7a-methyl-1H-inden-4-ol was converted to 1R-[1 alpha(R*,R*), 3a beta, 4 beta, 7a alpha]-octahydro-1-[1-methyl-2-(2,2,4,4-tetramethyl-1,3-dioxan-6-yl)ethyl]-7a-methyl-1H-inden-4-one, [α]$_D^{25}$ +38.12° (C, 0.522, EtOH).

EXAMPLE 22

Preparation of (1 alpha, 3 beta, 5Z, 7E, 23R)-9,10-Secocholesta-5,7,10(9)-triene-1,3-bis[(1,1-dimethylethyl)-dimethylsilyloxy]-23,25-diol-(1-methylethylidene)-cyclic acetal Following the procedure of example 11, 1R-[1 alpha (R*,R*), 3a beta, 4 beta, 7a alpha]-octahydro-1-[1-methyl-2-(2,2,4,4-tetramethyl-1,3-dioxan-6-yl)ethyl]-7a-methyl-1H-inden-4-one was converted to (1 alpha, 3 beta, 5Z,7E,23R)-9,10-secocholesta-5,7,10(9)-triene-1,3-bis[(1,1-dimethylethyl)-dimethylsilyloxy]-23,25-diol-(1-methylethylidene)-cyclic acetal.

EXAMPLE 23

Preparation of (1 alpha, 3 beta, 5Z,7E,23R)-9,10-Secocholesta-5,7,10(19)-triene-1,3,23,25-tetrol. (Syn. 1 alpha,23R,25-Trihydroxycholecalciferol)

Following the procedure of example 12, (1 alpha, 3 beta, 5Z,7E,23R)-9,10-secocholesta-5,7,10(9)-triene-1,3-bis[(1,1-dimethylethyl)-dimethylsilyloxy]-23,25-diol-(1-methylethylidene)-cyclic acetal was converted to (1 alpha, 3 beta, 5Z,7E,23R)-9,10-secocholesta-5,7,10(19)-triene-1,3,23,25-tetrol. (Syn. 1 alpha, 23R,25-trihydroxycholecalciferol), [α]$_D^{25}$ +24.55° (C, 0.5051, EtOH).

We claim:

1. A compound of the formula

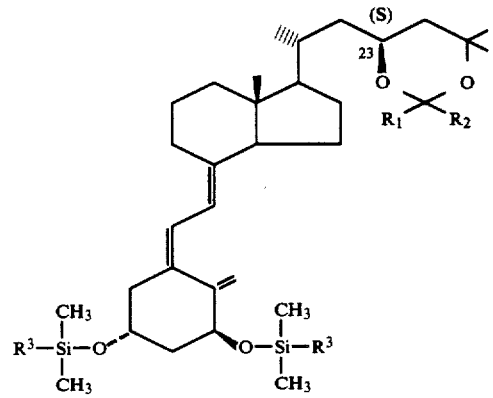

wherein R$_1$ and R$_2$ each independently are lower alkyl.

2. A compound in accordance with claim 1, (1 alpha, 3 beta, 5Z, 7E, 23S)-9,10-secocholesta-(4,7,10(9)-triene- 1,3-bis[1,1-dimethylethyl)-dimethylsilyloxy]-23,25-diol-(1-methylethylidene)-cyclic acetal.

3. A compound in accordance with claim 1, (1 alpha, 3 beta, 5Z, 7E, 23R)-9,10-secocholesta-4,7,10(9)-triene-1,3-bis[(1,1-dimethylethyl)-dimethylsilyloxy]-23,25-diol-(1-methylethylidene)-cyclic acetal.

4. A compound of the formula

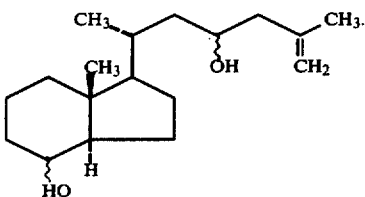

VII

5. A compound in accordance with claim 4 [1R-[alpha(R*,S*), 3a beta, 4 beta, 7a alpha]]-octahydro-1-(3-hydroxy-1,5-dimethyl-5-hexenyl)-7a-methyl-1H-inden-4-ol.

6. A compound in accordance with claim 4, [1R-[alpha(R*,R*), 3a beta, 4 beta, 7a alpha]]-octahydro-1-(3-hydroxy-1,5-dimethyl-5-hexenyl)-7a-methyl-1H-inden-4-ol.

7. A compound of the formula

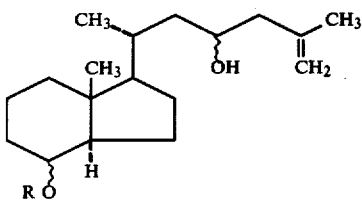

VII-A wherein R⁴ is tri-lower alkylsilyl, di-lower alkylarylsilyl, lower alkyldiarylsilyl, triarylsilyl.

8. A compound in accordance with claim 7 which is [1R-[1 alpha (R*,S*), 3a beta, 4 beta, 7a alpha]]-octahydro-1-(3-hydroxy-1,5-dimethyl-5-hexenyl)-7a-methyl-1H-inden-4-ol mono trimethylsilyl ether.

9. A compound in accordance with claim 7 which is [1R-[1 alpha (R*,R*), 3a beta, 4 beta, 7a alpha]]-octahydro-1-(3-hydroxy-1,5-dimethyl-5-hexenyl)-7a-methyl-1H-inden-4-ol mono trimethylsilyl ether.

10. A compound of the formula

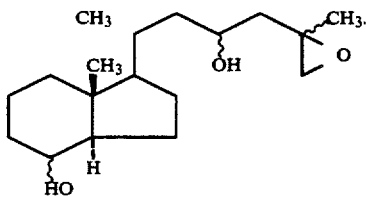

IX

11. A compound in accordance with claim 10 1R-[1alpha(R*,S*,R*),3a beta, 4 beta, 7a alpha]-octahydro-1-[3-hydroxy-1-methyl-4-(1-methyloxiranyl)butyl]-7a-methyl-1H-inden-4-ol or 1R-[1alpha(R*,S*,S*), 3a beta, 4 beta, 7a alpha-octahydro-1-[3-hydroxy-1-methyl-4-(1-methyloxiranyl)-butyl]-7a-methyl-1H-inden-4-ol.

12. A compound in accordance with claim 10, 1R-[1alpha(R*,R*,R*),3a beta, 4 beta, 7a alpha]-octahydro-1-[3-hydroxy-1-methyl-4-(1-methyloxiranyl)butyl]-7a-methyl-1H-inden-4-ol or 1R-[1alpha(R*,R*,S*), 3a beta, 4 beta, 7a alpha-octahydro-1-[3-hydroxy-1-meth-yl-4-(1-methyloxiranyl)-butyl]-7a-methyl-1H-inden-4-ol.

13. A compound of the formula

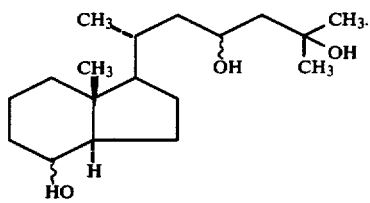

X

14. A compound in accordance with claim 13 [1R-[1alpha(R*,S*),3a beta, 4 beta, 7a alpha]]-octahydro-4-hydroxy-7a-methyl-1H-inden-1-yl)-1,6-dimethyl-2,4-hexanediol.

15. A compound in accordance with claim 13, [1R-[1alpha(R*,R*),3a beta, 4 beta, 7a alpha]]-octahydro-4-hydroxy-7a-methyl-1H-inden-1-yl)-1,6-dimethyl-2,4-hexanediol.

16. A compound of the formula

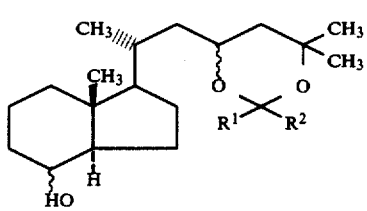

XII wherein R¹ and R² each independently is hydrogen, lower alkyl or aryl, or taken together are lower alkylene of from 3 to 6 carbon atoms.

17. A compound in accordance with claim 16, 1R-[1alpha(R*,S*), 3a beta, 4 beta, 7a alpha]-octahydro-1-[1-methyl-2-(2,2,4,4-tetramethyl-1,3-dioxan-6-yl)ethyl]-7a-methyl-1H-inden-4-ol.

18. A compound in accordance with claim 16, 1R-[1alpha(R*,R*), 3a beta, 4 beta, 7a alpha]-octahydro-1-[1-methyl-2-(2,2,4,4-tetramethyl-1,3-dioxan-6-yl)ethyl]-7a-methyl-1H-inden-4-ol.

19. A compound of the formula

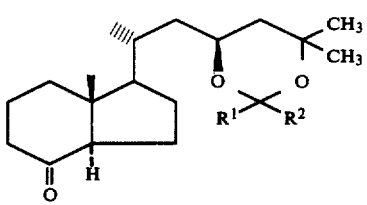

II wherein R¹ and R² each independently is hydrogen, lower alkyl or aryl or taken together are lower alkylene of from 3 to 6 carbon atoms.

20. A compound in accordance with claim 19, 1R-[1alpha(R*,S*), 3a beta, 4 beta, 7a alpha]-octahydro-1-[1-methyl-2-(2,2,4,4-tetramethyl-1,3-dioxan-6-yl)ethyl]-7a-methyl-1H-inden-4-one.

21. A compound in accordance with claim 19, 1R-[1alpha(R*,R*), 3a beta, 4 beta, 7a alpha]-octahydro-1-[1-methyl-2-(2,2,4,4-tetramethyl-1,3-dioxan-6-yl)ethyl]-7a-methyl-1H-inden-4-one.

22. A compound of the formula

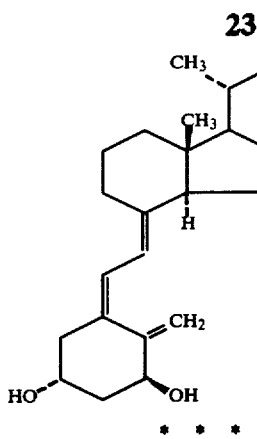 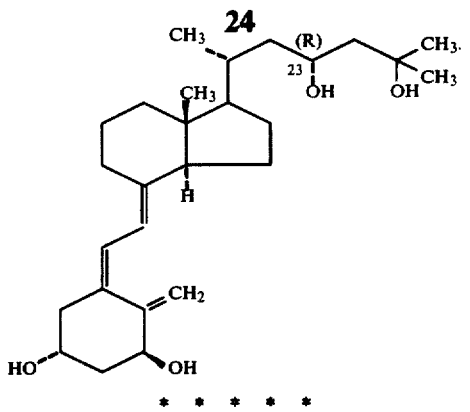

UNITED STATES PATENT AND TRADEMARK OFFICE
CERTIFICATE OF CORRECTION

PATENT NO. : 4,594,432

DATED : June 10, 1986

INVENTOR(S) : Enrico G. Baggiolini, Milan R. Uskokovic, Peter M. Wovkulich

It is certified that error appears in the above-identified patent and that said Letters Patent is hereby corrected as shown below:

In claim 10, formula IX

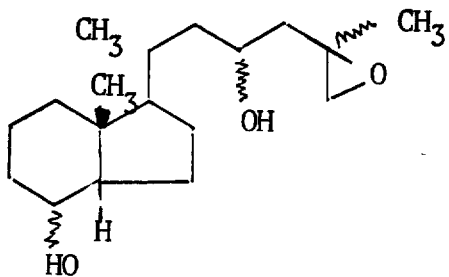

should be

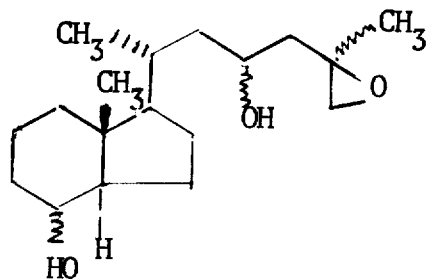

UNITED STATES PATENT AND TRADEMARK OFFICE
CERTIFICATE OF CORRECTION

PATENT NO. : 4,594,432
DATED : June 10, 1986
INVENTOR(S) : Enrico G. Baggiolini, Milan R. Uskokovic et al It is certified that error appears in the above-identified patent and that said Letters Patent is hereby corrected as shown below:

In claim 22, delete the formula from column 24.

Signed and Sealed this

Fifth Day of July, 1988

*Attest:*

DONALD J. QUIGG

*Attesting Officer*　　　*Commissioner of Patents and Trademarks*